(12) United States Patent
Dietrich

(10) Patent No.: US 6,776,615 B2
(45) Date of Patent: Aug. 17, 2004

(54) TWEEZERS

(76) Inventor: Herbert Dietrich, Hauptplatz 6, A-2500 Baden (AT)

( * ) Notice: Subject to any disclaimer, the term of this patent is extended or adjusted under 35 U.S.C. 154(b) by 0 days.

(21) Appl. No.: 09/953,017

(22) Filed: Sep. 14, 2001

(65) Prior Publication Data

US 2002/0127514 A1 Sep. 12, 2002

(30) Foreign Application Priority Data

Sep. 15, 2000 (AT) .......................................... 1580/2000

(51) Int. Cl.$^7$ ................................................ A61C 3/14
(52) U.S. Cl. ......................................... 433/159; 81/419
(58) Field of Search ................................ 433/159, 160, 433/4; 81/419, 420, 424.5

(56) References Cited

U.S. PATENT DOCUMENTS

| | | | | |
|---|---|---|---|---|
| 1,064,404 A | * | 6/1913 | Walker ........................... 433/4 |
| 1,268,922 A | * | 6/1918 | Bryan ........................ 72/390.5 |
| 1,518,021 A | * | 12/1924 | Truxillo ...................... 433/159 |
| 3,747,648 A | * | 7/1973 | Bauer .......................... 606/107 |
| 5,036,733 A | * | 8/1991 | Tiholiz et al. ................. 76/119 |
| 5,217,464 A | * | 6/1993 | McDonald ................... 606/107 |
| 5,257,558 A | * | 11/1993 | Farzin-Nia et al. .......... 433/159 |
| 6,095,815 A | * | 8/2000 | Mueller ....................... 433/159 |

* cited by examiner

Primary Examiner—John J. Wilson
(74) Attorney, Agent, or Firm—Reed Smith LLP

(57) ABSTRACT

Tweezers for holding strip-shaped or thread-shaped material with particularly abrasive characteristics are disclosed, for example, for dental purposes, wherein clamping elements, particularly in the shape of rods, are arranged in the area of the free end of each of the two legs of the tweezers, and wherein, in the closed position of the tweezers, at least one clamping element arranged at a leg contacts two clamping elements arranged at a distance from one another at the other leg or engages in a recess located in the latter.

7 Claims, 3 Drawing Sheets

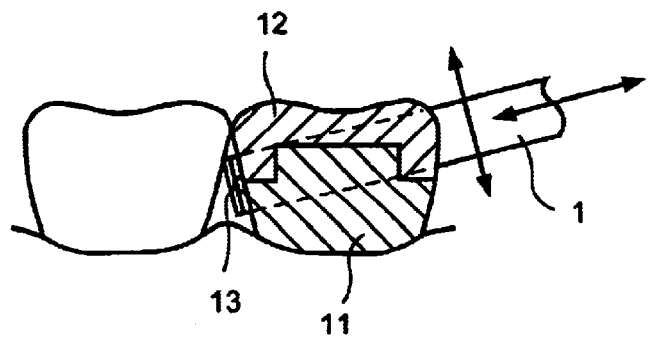
F I G. 1
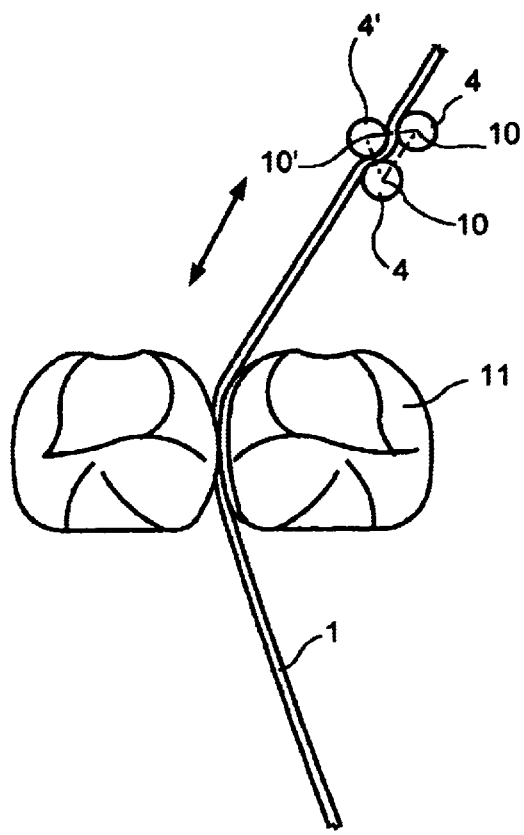
F I G. 2

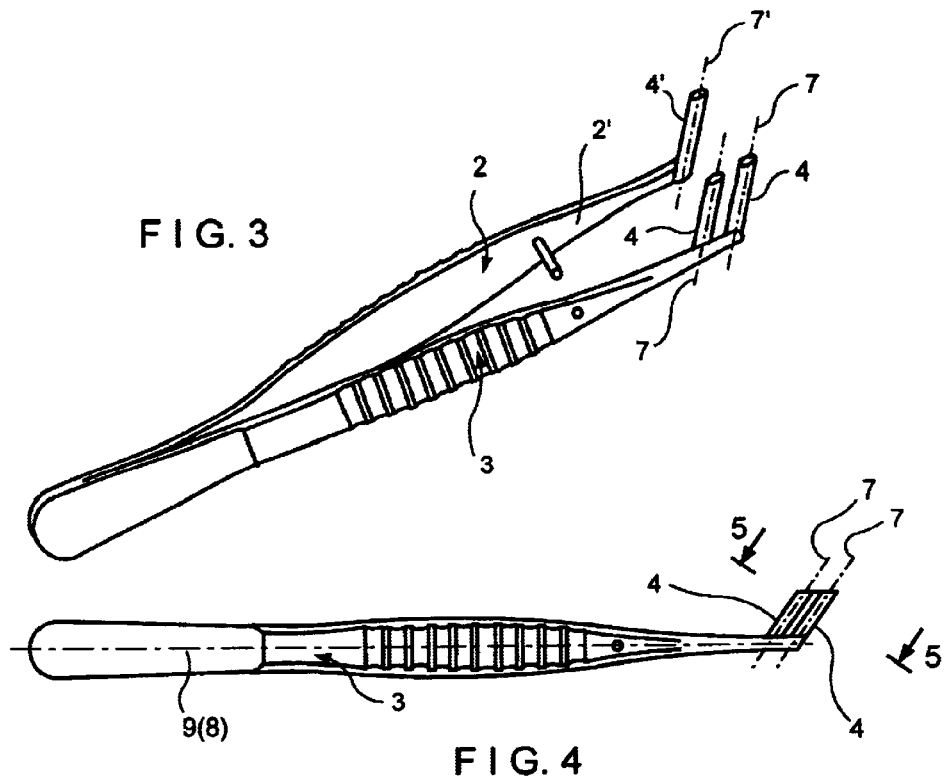
FIG. 3
FIG. 4
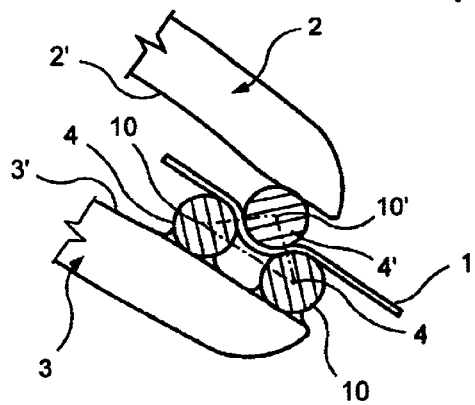
FIG. 5
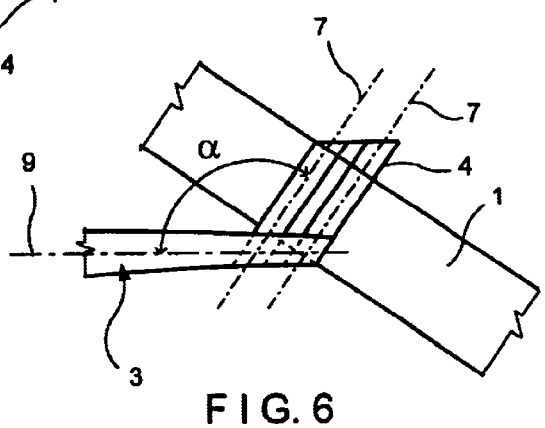
FIG. 6

TWEEZERS

CROSS REFERENCE TO RELATED APPLICATIONS

This application claims priority of Austrian Application No. A 1580/2000, filed Sep. 15, 2000, the complete disclosure of which is hereby incorporated by reference.

FIELD OF THE INVENTION

The invention is directed to tweezers for holding strip-shaped or thread-shaped material with particularly abrasive characteristics, for example, for dental purposes. During intraoral working of tooth fillings and with dental restorations, particularly crowns, which are attached by adhesion, the use of commercially available polishing strips and finishing strips having a width of 5–6 mm as strip-shaped material causes difficulties, primarily with respect to space, especially when a dental dam through which a tooth to be treated protrudes is located inside the oral cavity. This is also true of strips of half-width (2.5–6 mm) and for thread-shaped material.

OBJECT AND SUMMARY OF THE INVENTION

It is one of the objects of the invention to remedy this difficulty in that clamping elements, particularly in the shape of rods, are arranged in the area of the free end of each of the two sides or legs of the tweezers, wherein, in the closed position of the tweezers, at least one clamping element arranged at a leg contacts two clamping elements arranged at a distance from one another at the other leg or engages in a recess located in the latter.

In particular, in accordance with the invention, tweezers for holding strip-shaped or thread-shaped material with particularly abrasive characteristics, for example, for dental purposes, particularly in the shape of rods, are arranged in the area of the free end of each of the two legs of the tweezers, wherein in the closed position of the tweezers, at least one clamping element arranged at a leg contacts two clamping elements arranged at a distance from one another at the other leg or engages in a recess located in the latter.

By using the tweezers outfitted according to the invention, it is possible to hold the strip-shaped or thread-shaped material, for example, a polishing strip located inside the oral cavity, without difficulty so that a strip, which can also be made from metal, can be moved back and forth in the gap between two adjacent teeth or on the lateral surface of a tooth in order to polish the surface. The tweezers make it possible to hold the strip-shaped or thread-shaped material without difficulty by means of the clamping elements without the material, e.g., the polishing strip, being bent by the cooperating clamping elements. Strips of half-width (2.5–3 mm) can be introduced into the interdental space below the contact point of adjacent teeth and can be moved without difficulty in the longitudinal direction of the strip and also transverse to the strip, so that every point on the tooth can be reached by the strip. The working part of the polishing strip or thread can be varied continuously in length (working length) by letting go and then holding again with the tweezers. Therefore, it is not necessary to exchange the strip or thread in the course of a polishing or working process; rather, the entire length of the strip or thread is available for working. Therefore, use of the tweezers according to the invention also makes it possible to economize on strips or threads in dental practice.

In a further development of the invention, the clamping elements are constructed as cylinders, preferably with circular cross section, which are arranged axially parallel to one another. They can be fastened to the inner side of the legs of the tweezers by gluing, soldering or welding. The cylinders can also be flattened toward the outer side of the tweezers. However, the cylinders could also have an elliptical cross section in a section vertical to their axis. The cylinders can also be worked out of the material of the tweezers directly, in which case the clamping elements need not be fastened by special fastening means or by gluing, soldering or welding.

In a further embodiment form, the clamping elements of the tweezers according to the invention can be arranged in such a way that they project above the legs of the tweezers on at least one side. In this way, it can be ensured that the clamping elements have sufficient free length to clamp strip-shaped material over its entire width, so that the strip-shaped material is clamped without being damaged.

Handling is improved in a further development of the invention when the longitudinal axis of the rod-shaped clamping elements encloses an obtuse angle with the longitudinal axis of the legs of the tweezers. However, constructions with an acute angle or right angle can also be used. In poorly accessible locations, the angle can be between 75° and 90°.

In another possible embodiment form of the clamping elements, the latter terminate flush with the longitudinal boundaries of the legs of the tweezers. This embodiment form dispenses with clamping elements projecting over the tweezers.

In order to increase friction between the clamping elements and the strip-shaped or thread-shaped material, it is advisable when the outer surface of the clamping elements has a friction coating, e.g., diamond powder, at least in the area of contact with the strip-shaped or thread-shaped material, as is provided in a preferred embodiment form of the tweezers according to the invention. The parts of the outer surface of the clamping elements which do not come into contact with the strip-shaped or thread-shaped material during the clamping process and the plane end faces of the clamping elements advisably do not have a friction coating and, in particular, are polished.

The arrangement of the clamping elements can be carried out in such a way that in the clamping position of the tweezers the centers of the circular cross sections form corner points of an isosceles right-angled triangle in an imaginary section through the clamping cylinder normal to the axis. The cylinder diameters of the clamping elements provided on tweezers can also differ from one another.

The invention will be described more fully in the following by way of example with reference to the drawing.

BRIEF DESCRIPTION OF THE DRAWINGS

In the drawings:

FIG. 1 shows a tooth in longitudinal section adjacent to a tooth shown in a front view;

FIG. 2 is a top view of FIG. 1;

FIG. 3 shows an embodiment form of tweezers according to the invention in a three-dimensional view;

FIG. 4 shows the tweezers according to FIG. 3 in a side view;

FIG. 5 shows a section along line V—V in FIG. 4;

FIG. 6 shows the front end of tweezers with polishing strips clamped between the legs;

DESCRIPTION OF THE PREFERRED EMBODIMENTS

Figure 7:
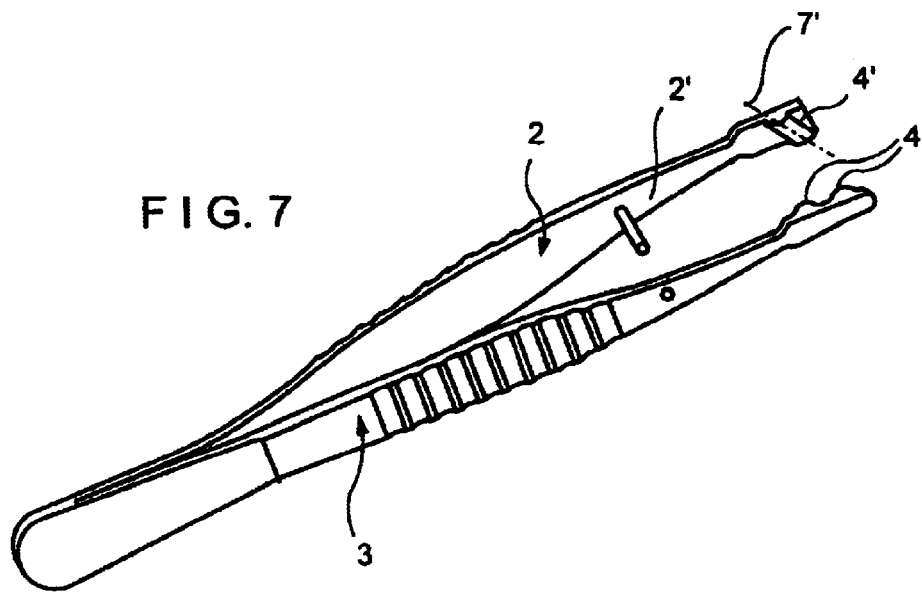
FIG. 7 is a three-dimensional view showing an embodiment form of tweezers according to the invention that is modified from the view in FIG. 3.
Figure 8:
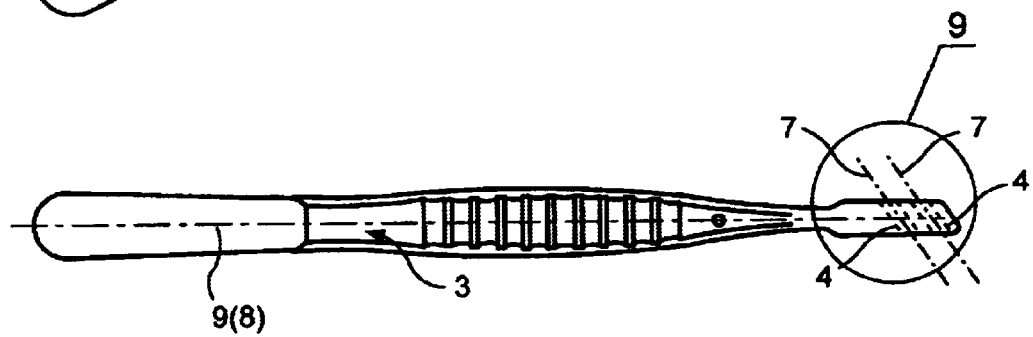
FIG. 8 is a side view of the tweezers shown in FIG. 7.
Figure 9:
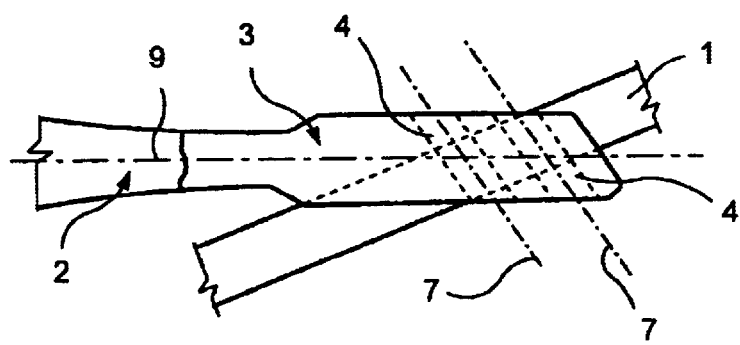
FIG. 9 shows the detail from FIG. 8, designated by reference number 9, in an enlarged view compared with FIG. 8, wherein a polishing strip is shown in a position in which it is clamped by the legs of the tweezers.

A polishing strip such as is used in dentistry is designated by 1 in the drawing as an example of the strip-shaped or thread-shaped material. The tooth 11 to be polished by means of the polishing strip 1 is provided with a dental restoration 12 in the form of a crown which is fastened by adhesion to the tooth stump. When gluing, glue can exit laterally from the clamping joint and forms a bead 13 which must be removed in order to achieve a smooth lateral tooth surface. The polishing strip 1 is used to remove such irregularities. Tweezers are advisably used for holding and moving the polishing strip 1, wherein clamping elements 4, 4' are arranged in the area of the free end of each leg 2, 3 of the tweezers. These clamping elements are constructed in a rod-shaped manner in the embodiment examples (FIGS. 3 to 9) shown in the drawing. The polishing strips can be made from plastic or metal (metal matrix strips). The thickness is preferably on the order of magnitude of 40 µm.

In the closed position of the tweezers, a clamping element 4' arranged at the leg 2 of the tweezers contacts two clamping elements 4 arranged at a distance from one another at the other leg 3. The clamping element which is provided at one leg and constructed in the manner of a knob (ball joint), for example, could also engage in a congruent recess arranged at the other leg in a manner not shown in the drawing. With an appropriate design of the clamping elements, it is also possible in this case to prevent damage to the surface of the strip-shaped material, e.g., by formation of a fold in the clamping area.

In the present embodiment examples, the clamping elements 4, 4' are constructed as circular cylinders arranged with axes parallel to one another. The fastening of the cylinders to the legs 2 and 3 can be carried out by gluing, soldering or welding to the inner side 2', 3' of the legs 2, 3 of the tweezers. However, screw fastening could also be provided. The cylinders could also be attached to the free ends of the legs in the manner of carriers or slides, in which case the ends of the legs could engage in a longitudinal slot which is arranged at the cylindrical clamping element proceeding from a side surface of the clamping element.

In the embodiment form according to FIGS. 3 and 4, the clamping elements on one side project above the legs of the tweezers. The arrangement could also be carried out in such a way that the clamping elements project above the legs of the tweezers on both sides, preferably to ⅔ of its length on one side and to ⅓ of its length on the other side. In contrast, in the embodiment form according to FIGS. 7 to 9, the clamping elements 4, 4' terminate flush with the longitudinal boundaries of the legs 2, 3 of the tweezers.

In the embodiment forms shown herein, the longitudinal axis 7 and 7' of the rod-shaped clamping elements 4, 4' enclose an obtuse angle a with the longitudinal axis 8 and 9 of the legs 2, 3, respectively.

In order to increase the friction between the clamping elements and the thread-shaped or strip-shaped material (polishing strip 1), it is advisable to provide the outer surface of the clamping elements 4, 4' with a friction coating at least in the area of contact with the polishing strip 1; in the other areas, the clamping elements can be polished. A suitable friction coating is, e.g., diamond powder which is applied to the surface of the clamping elements.

As is shown in FIGS. 2 and 5, the centers 10, 10' of the circular cross sections form the corner points of an isosceles right-angled triangle in the clamping position in a section through the clamping cylinders normal to the axis. The cylinder cross sections can also be elliptical in a manner which is not shown.

With respect to the arrangement of the clamping elements on the legs of the tweezers, right-hand and left-hand tweezers can be produced. The end faces of the clamping elements should be polished and should therefore not have a friction coating. This ensures that less experienced users of the tweezers will not scratch the surrounding hard tooth structure so that the surface of the tooth remains smooth.

While the foregoing description and drawings represent the present invention, it will be obvious to those skilled in the art that various changes may be made therein without departing from the true spirit and scope of the present invention.

What is claimed is:

1. Tweezers for holding strip-shaped or thread-shaped material with particularly abrasive characteristics including for dental purposes, comprising:

clamping elements in the shape of rods, being arranged in the area of a free end of each of two legs of the tweezers;

at least one clamping element arranged at a leg so that the at least one clamping element contacts two other clamping elements arranged at a distance from one another at the other leg in a closed position of the tweezers; wherein the clamping elements are constructed as cylinders, with circular cross section, which are arranged axially parallel to one another and are fastened to the inner side of the legs of the tweezers by gluing, soldering or welding.

2. Tweezers according to claim 1, wherein the clamping elements project above the legs of the tweezers on at least one side.

3. Tweezers according to claim 1, wherein the longitudinal axis of the rod-shaped clamping elements encloses an obtuse angle with the longitudinal axis of the legs.

4. Tweezers according to claim 1, wherein the clamping elements at both ends terminate flush with the longitudinal boundaries of the legs of the tweezers.

5. Tweezers according to claim 1, wherein the outer surface of the clamping elements has a friction coating, at least in the area of contact with the strip-shaped or thread-shaped material.

6. Tweezers according to claim 5, wherein the friction coating is a diamond powder.

7. Tweezers according to claim 1 wherein in the clamping position, the centers of the circular cross sections form corner points of an isosceles right-angled triangle in a section through the clamping cylinder normal to the axis.

* * * * *